United States Patent [19]

Uyeo et al.

[11] Patent Number: 5,064,954
[45] Date of Patent: Nov. 12, 1991

[54] PROCESS FOR PRODUCING HALOMETHYLCARBAPENEMS

[75] Inventors: Shoichiro Uyeo, Kyoto; Mitsuru Imuta, Osaka; Hisao Ona, Nara; Hikaru Itani, Osaka, all of Japan

[73] Assignee: Shionogi & Co., Ltd., Osaka, Japan

[21] Appl. No.: 594,942

[22] Filed: Oct. 10, 1990

[51] Int. Cl.$^5$ .................................... C07D 487/04
[52] U.S. Cl. ................................................ 540/302
[58] Field of Search ....................................... 540/302

[56] References Cited

U.S. PATENT DOCUMENTS 4,298,741  11/1981  Christsen et al. ............. 540/302
4,310,538  1/1982  Christsen et al. ............. 540/302

FOREIGN PATENT DOCUMENTS 0185315  6/1986  European Pat. Off. .

OTHER PUBLICATIONS

CA113:1149371 "Preparation of Azetidinone Intermediates for Carbapenems" Uyeo, Shoichiro (1990).

*Primary Examiner*—Mukund J. Shah
*Assistant Examiner*—Jyothsna Venkat
*Attorney, Agent, or Firm*—Birch, Stewart, Kolasch & Birch

[57] ABSTRACT

A functionallized intermediate for antibacterial carbapenems, 2-halomethylcarbapenem (III) is effectively synthesized by treating 2-hydroxymethylcarbapenem (I) with a phosphorylating reagent to give 2-phosphoryloxymethylcarbapenem (II) and then treating this product with a halogenating reagent. Some carbapenems derived from the intermediate are also disclosed.

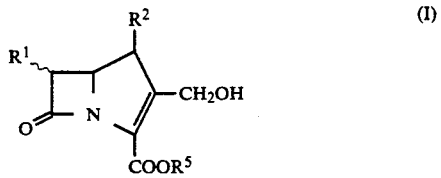

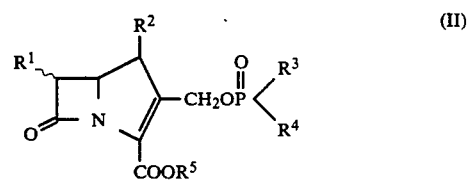

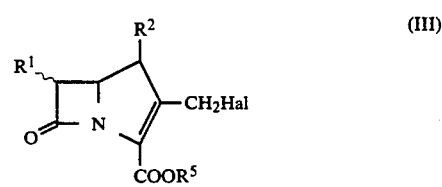

wherein,
$R^1$ is hydrogen or substituted or unsubstituted alkyl;
$R^2$ is hydrogen or substituted or unsubstituted alkyl;
$R^3$, $R^4$ is halogen or substituted or unsubstituted alkoxy or aryloxy;
$R^5$ is hydrogen or carboxy protecting group; and
Hal is halogen.

9 Claims, No Drawings

PROCESS FOR PRODUCING HALOMETHYLCARBAPENEMS

This invention provides a prescription for synthesizing 2-halomethylcarbapenem compound (III) never appeared in the prior arts. It further provides practical production of carbapenem compounds.

TECHNICAL BACKGROUND

2-Toluenesulfonyloxymethylcarbapenem (2) disclosed in European Patent Application No. 0 185 315 Example 4, Step 4 said to be prepared by toluenesulfonating 2-hydroxymethylcarbapenem (1) does not accompany any physical constant. Various compounds said to be prepared by the same patent publication, Example 4, step B to Example 6 starting from the said toluenesulfonate also do not accompany any physical constant.

The present inventor traced this Example 4 to obtain a product in a high yield of 89%. It was not said p-toluenesulfonate but 2-(2-allyloxycarbonyl-3,3-methylene-4-methyl-1-pyrroline-5-yl)-3-hydroxybutanoic acid lactone (3).

Further, any betalactam compound, e.g., objective trimethylsilylated compound (2), was not detected in the reaction mixture, even when the hydroxy of the side chain at position 6 of compound (2) was protected with trimethylsilyl.

Therefore, toluenesulfonate (2) and compounds derived therefrom seem to be an illusion including structure nominations, productions, and disclosure of analogous compounds.

PROBLEMS TO BE SOLVED

In place of sulfonyl unproducible by the prior art, introduction of a practical functional group is the problem to be solved.

Then the inventor tried to use halogen atom as the leaving group. A conventional substitution of hydroxy with halogen failed. For example, the halogenation of 2-hydroxymethylcarbapenem (1) with thionyl chloride did not give 2-chloromethylcarbapenem (2) but gave 2,2-methylene-3-chlorocarbapenam (3).

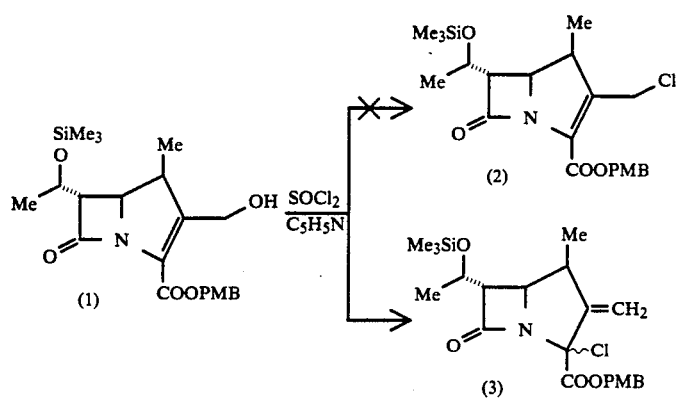

EMBODIMENT OF THIS INVENTION

This invention comprises Step 1 producing 2-phosphoryloxymethylcarbapenem (II) by treating 2-hydroxymethylcarbapenem (I) with a phosphorylating reagent and Step 2 producing 2-halomethylcarbapenem (III) by treating 2-phosphoryloxymethylcarbapenem (II) with a halogenating reagent.

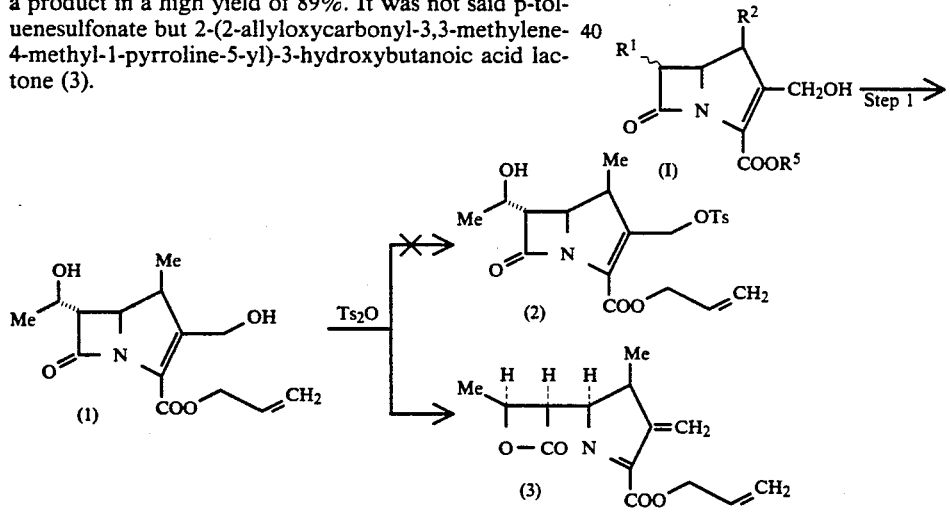

-continued

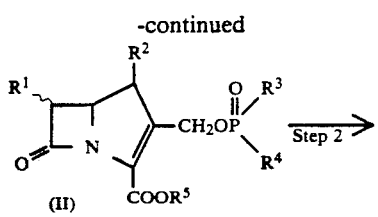

wherein,

R¹ is hydrogen or substituted or unsubstituted alkyl;
R² is hydrogen or substituted or unsubstituted alkyl;
R³, R⁴ is halogen or substituted or unsubstituted alkoxy or aryloxy;
R⁵ is hydrogen or carboxy protecting group; and
Hal is halogen.

The phosphorylation of allyl alcohol followed by halogenation to give allyl halide is found in Synthesis, 1984, 841-842. However, any halogen substitution of weakly electrophilic phosphoryloxy as the leaving group has never been found in the betalactam literatures.

PROCESS OF THIS INVENTION

Step 1: Phosphorylation

2-Hydroxymethylcarbapenem (I) is treated with a phosphorylating reagent in the presence of an acid scavenger to give 2-phosphoryloxymethylcarbapenem (II) in high yield.

Namely, 2-hydroxymethylcarbapenem (I) is treated with a phosphorylating reagent (a reactive derivative of phosphoric acid) in the presence of an acid scavenger (dimethylaminopyridine, etc.) in an inert solvent (dichloromethane, etc.) at −60° to −20° C. for 30 minutes to 3 hours to give 2-phosphoryloxymethylcarbapenem (II) in high yield.

The said reactive derivative of phosphoric acid is preferably a halogenide of phosphoric acid derivatives in which 2 of hydroxys in phosphoric acid is substituted by halogen, substituted or unsubstituted alkoxy or aryloxy. Said acid scavenger is inorganic base (oxide, hydroxide, carbonate, bicarbonate, etc. of alkali metal, alkaline earth metal, etc.), organic base (tertiary amine, aromatic base, etc.), oxirane (alkylene oxide, aralkylene oxide, etc.), adsorbent (celite, etc.).

This reaction is carried out by treating 2-hydroxymethylcarbapenem (I) with 1 to 5 equivalents of a phosphorylating reagent and an acid scavenger 0 to 2 equivalents preferably in an aprotic solvent.

Step 2: Substitution with Halogen

2-Phosphoryloxymethylcarbapenem (II) is treated with a halogenating reagent to give 2-halomethylcarbapenem (III) in high yield.

Thus the reaction of 2-phosphoryloxymethylcarbapenem (II) with a halogenating reagent (halide of a light metal, e.g., alkali metal, alkaline earth metal; silyl halide, e.g., tri-lower alkyl-silyl halide, di-lower alkylsilyl dihalide, mono-lower alkylsilyl halide, silane tetrahalide; stannic halide, e.g., tri-lower alkylstannic halide, di-lower alkylstannic dihalide, silane tetrahalide, at −40° C. to room temperature for 30 minutes to 3 hours to give 2-halomethylcarbapenem (III) in high yield.

REACTION CONDITIONS

The said syntheses each is usually carried out at −60° C. to 50° C., especially −50° C. to 40° C., for 10 minutes to 15 hours. If the product is stable in the reaction mixture, the latter may be left standing for a longer time. These may be carried out keeping dry, in an inert gas, in a solvent with stirring, or the like conventional condition.

The reaction solvent for this invention can be a hydrocarbon (pentane, hexane, octane, benzene, toluene, xylene, etc.), halohydrocarbon (dichloromethane, chloroform, carbon tetrachloride, dichloroethane, trichloroethane, chlorobenzene, etc.), ether (diethyl ether, methyl isobutyl ether, dioxane, tetrahydrofuran, etc.), ketone (acetone, methyl ethyl ketone, cyclohexanone, etc.), ester (ethyl acetate, isobutyl acetate, methyl benzoate, etc.), nitrohydrocarbon (nitromethane, nitrobenzene, etc.), nitrile (acetonitrile, benzonitrile, etc.), amide (formamide, acetamide, dimethylformamide, dimethylacetamide, hexamethylphosphorotriamide, etc.), sulfoxide (dimethyl sulfoxide, etc.), carboxylic acid (formic acid, acetic acid, propionic acid, etc.), organic base (diethylamine, triethylamine, pyridine, picoline, collidine, quinoline, etc.), or the like industrial solvent or a mixture.

WORK UP

The objective products can be recovered from the reaction mixture after removing contaminants (unreacted starting material, by-products, solvents, etc.) by a conventional method (extracting, evaporating, washing, concentrating, precipitating, filtrating, drying, etc.) and purified by a usual work up (adsorbing, eluting, distilling, precipitating, separating, chromatographying, etc.).

EXPLANATION OF SYMBOLS

In the formulas, R¹ is hydrogen or substituted or unsubstituted alkyl being a 6-substituent of penem or carbapenem compounds. Preferable are hydrogen and 1C to 10C 1-(hydroxy or halo)-alkyl. Representative are 1C to 8C alkyl (e.g., methyl, ethyl, propyl), 1C to 8C hydroxyalkyl (e.g., hydroxymethyl, 1-hydroxyethyl, 1-hydroxypropyl, 2-hydroxyisopropyl), 1C to 8C haloalkyl (e.g., fluoromethyl, chloromethyl, 1-fluoroethyl, 2-fluoroisopropyl, trifluoromethyl), 4C to 8C dioxolyl (e.g., 2-oxo-4-alkyl (e.g., methyl, ethyl, propyl)dioxolyl).

The hydroxy in R¹ may be protected by a group which may be removed afterwards in a step up to the final objective compound. Representative are easily removable ester forming groups [for example, 1C to 11C carboxylic acyl (e.g., lower alkanoyl, aroyl), 2C to 10C carbonic acyl (e.g., lower alkoxycarbonyl, chloroalkoxycarbonyl, benzyloxycarbonyl, p-nitrobenzyloxycarbonyl, p-methoxybenzyloxycarbonyl, o-nitrobenzyloxycarbonyl, allyloxycarbonyl)], 2C to 8C ether forming groups (e.g., methoxymethyl, methoxyethoxymethyl, tetrahydrofuranyl, tetrahydropyranyl) 3C to 18C hydrocarbylsilyl (e.g., trimethylsilyl, triethylsilyl, dimethylphenylsilyl, diphenylmethylsilyl, diphenyl-tert-butylsilyl, dimethyl-tert-pentylsilyl), and 7C to 19C reactive aralkyl (e.g., triphenyl-methyl).

Especially preferable alkyl or substituted alkyl as $R^2$ is 1C to 8C alkyl. Representative are 1C to 3C alkyl (e.g., methyl, ethyl, propyl), 1C to 5C haloalkyl (e.g., fluoro alkyl, chloroalkyl, bromoalkyl, 2C to 5C carbon substituted alkyl (e.g., cyanoalkyl, carbamoylalkyl, carboxyalkyl, protected carboxyalkyl, alkenyl, alkinyl), 1C to 5C nitrogen substituted alkyl (e.g., aminoalkyl, alkanoylaminoalkyl, aroylaminoalkyl, ureidoalkyl, formimidoylalkyl), 1C to 5C oxygen substituted alkyl (e.g., hydroxyalkyl, alkanoyloxyalkyl, carbamoyloxyalkyl, isohydroxyalkyloxyalkyl, aminoalkoxyalkyl, haloalkoxyalkyl), and 1C to 5C sulfur substituted alkyl (e.g., alkylthioalkyl, aminoalkylthioalkyl, hydroxyalkylthioalkyl, haloalkylthioalkyl, alkylsulfinylalkyl, aminoalkylsulfinylalkyl, hydroxyalkylsulfinylalkyl, haloalkylsulfinylalkyl, alkylsulfonylalkyl, aminoalkylsulfonylalkyl, hydroxyalkylsulfonylalkyl, haloalkylsulfonylalkyl). The said group having hydroxy may optionally have a hydroxy protecting group as described in the paragraph for $R^1$ group.

Representative substituent in alkoxy or aryloxy as $R^3$ or $R^4$ includes alkyl, alkoxy, halogen, nitro, cyano, etc.

The carboxy protective group $R^5$ is a 1C to 19C carboxy protecting group introducible and removable without adverse effect on other part of the molecule, the protective groups for medical use (i.e., a pharmaceutically acceptable salt or ester forming group), or a salt forming carboxy protecting group known in penicillin and cephalosporin chemistry.

Representative carboxy protective groups $R^5$ are, for example, 1C to 8C alkyl (e.g., methyl, methoxymethyl, ethyl, ethoxymethyl, iodoethyl, propyl, isopropyl, butyl, isobutyl, ethoxyethyl, methylthioethyl, methanesulfonylethyl, trichloroethyl, tert-butyl), 3C to 8C alkenyl (e.g., propenyl, allyl, prenyl, hexenyl, phenylpropenyl, dimethylhexenyl), 7C to 19C aralkyl (e.g., benzyl, methylbenzyl, dimethylbenzyl, methoxybenzyl, ethoxybenzyl, nitrobenzyl, aminobenzyl, diphenylmethyl, phenylethyl, trityl, di-tert-butylhydroxybenzyl, phthalidyl, phenacyl), 6C to 12C aryl (e.g., phenyl, tolyl, diisopropylphenyl, xylyl, trichlorophenyl, pentachlorophenyl, indanyl), 1C to 12C amino (a group for forming an ester with e.g., acetone oxime, acetophenone oxime, acetaldoxime, N-hydroxysuccinimide, N-hydroxyphthalimide), 3C to 12C hydrocarbylsilyl (e.g., trimethylsilyl, dimethylmethoxysilyl, tert-butyldimethylsilyl), and 3C to 12C hydrocarbylstannyl (e.g., trimethylstannyl), 1C to 10C alkanoyl (e.g., formyl, acetyl, propionyl, octanoyl), 1C to 12C sulfonic acyl (e.g., methanesulfonyl, ethanesulfonyl, benzenesulfonyl, toluenesulfonyl, bromobenzenesulfonyl), phosphonic acyl (e.g., dimethylphosphoryl, diethylfphosphoryl, diphenylphosphoryl), and mineral acid acyl (e.g., chloro, sulfo, phospho). This carboxy protective group is eliminated in the course up to the final objective compounds. So, the structure itself has no specific role as far as the protection can be effected. A wide variety of equivalent groups (e.g., amide, carbonic or carboxylic acid anhydride) are thus available.

The representative salt forming carboxy protective groups $R^5$ give salts of a light metal of group I to III, period 2 to 4 of the periodical table (e.g., lithium, sodium, potassium, magnesium, calcium, aluminum), 1C to 12C alkylamine (e.g., trimethylamine, triethylamine, methylmorpholine), and 4C to 9C aromatic base (e.g., pyridine, collidine, picoline, quinoline, dimethylaniline).

The pharmaceutically acceptable ester forming group $R^5$ shows antibacterial activity on enteral or parenteral administration. Representative are optionally substituted 2C to 15C 1-oxygen substituted alkyl {for example, straight, branched, cyclic or partly cyclic alkanoyloxyalkyl (e.g., acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl), 3C to 15C alkoxycarbonyloxyalkyl (e.g., ethoxycarbonyloxyethyl, isopropoxycarbonyloxyethyl, isopropoxycarbonyloxypropyl, tert-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl), 2C to 8C alkoxyalkyl (e.g., methoxymethyl, methoxyethyl), 4C to 8C 2-oxacycloalkyl (e.g., tetrahydropyranyl, tetrahydrofuranyl), and the like}, 8C to 12C substituted aralkyl (e.g., phenacyl, phthalidyl), 6C to 12C aryl (e.g., phenyl, xylyl, indanyl), and 2C to 12C alkenyl (e.g., allyl, oxodioxolylmethyl).

SCOPE OF SYMBOLS

The alkyl part of the said groups is optionally substituted straight, branched, or cyclic alkyl. Representative are 1C to 12C alkyl, e.g., methyl, ethyl, propyl, isopropyl, cyclopropyl, butyl, isobutyl, tert-butyl, cyclobutyl, cyclopropylmethyl, pentyl, isopentyl, neopentyl, cyclopentyl, cyclopropylethyl, hexyl, cyclohexyl, cyclopentylmethyl, heptyl, cycloheptyl, cyclopentylethyl, cyclohexylmethyl, octyl, cyclooctyl, cyclohexylethyl, nonyl, dodecyl, and the like. These may be unsaturated or substituted by a group as given below.

The aralkyl part is the combined alkyl part and aryl part. Representative are up to 14C aralkyl, e.g., benzyl, phenylethyl, phenylpropyl, phenylisopropyl, diphenylmethyl, methoxydiphenylmethyl, naphthylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl, quinolylmethyl, and the like. These may be substituted by a group as given below.

The acyl part is preferably up to 14C acyl being carboxylic acyl, e.g., optionally substituted straight, branched or cyclic alkanoyl, optionally substituted and monocyclic or dicyclic carbo- or heterocyclic aroyl, aralkanoyl, arylalkenoyl), sulfonic acyl (e.g., alkylsulfonyl, arylsulfonyl), carbonic acyl (e.g., carbamoyl, carbalkoxy, carboaralkoxy), sulfo, or the like.

The aryl part can be 5 to 6 membered monocyclic or dicyclic and carbocyclic or oxygen, nitrogen, and/or sulfur heterocyclic aryl and may have a substituent as given above. Representative are up to C10 aryl, e.g., phenyl, tetralinyl, naphthyl, indanyl, indenyl, furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuyl, benzothienyl, benzoimidazolyl, benzothiazolyl, benzopyrazinyl, quinolyl, pyridopyridyl, and the like. These may be substituted by a group as given below.

The representative substituent to be bound to the said groups can be a carbon function (e.g., straight, branched, or cyclic alkyl, alkenyl, alkinyl, aralkyl, aryl, heterocyclic group, carboxylic acyl, carbamoyl, carboxy, protected carboxy, cyano), a nitrogen function (e.g., amino, acylamino, guanidinyl, ureido, alkylamino, dialkylamino, isothiocyano, isocyano, nitro, nitroso), an oxygen function (e.g., hydroxy, alkoxy, aryloxy, heterocyclyl-oxy, cyanato, oxo, carboxylic acyloxy, sulfonic acyloxy, phosphoric acyloxy), a sulfur function (e.g., mercapto, alkylthio, alkylsulfonyl, arylthio, arylsulfonyl, heterocyclylthio, heterocyclylsulfonyl, acylthio, thioxo, sulfo, sulfamoyl), halogen (e.g. fluorine, chlorine, bromine, iodine), a silyl function (e.g., trialkylsilyl, dialkylalkoxysilyl), or a stannyl function (e.g., trialkylstannyl).

A USE OF COMPOUND (III)

There is no closely related prior art to the novel compound, 2-halomethylcarbapenem (III). Treatment of it with aromatic base or amine gives 2-substituted methylcarbapenem (IV) which is a novel antibacterial stable against human renal betalactamase, etc.

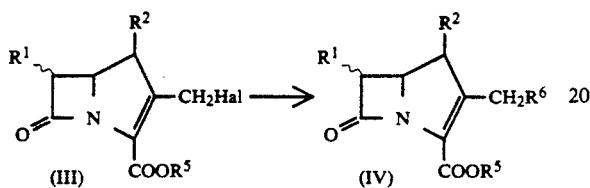

(wherein $R^1$, $R^2$, and Hal are as defined above, $R^5$ is as above or a negative charge with counter-ion; $R^6$ is neutral or positive charged nucleophilic group)

Representative $R^6$ is quaternary arylinio, e.g., optionally substituted thiazolyl, pyridyl, where the substituent can be alkyl (e.g., methyl, ethyl), aminomethyl, formamidomethyl), alkylene (e.g., dimethylene, trimethylene), alkanoyl (e.g., formyl, acetyl, propionyl), carbamoyl, heterocyclyl (e.g., oxazolyl, triazolyl, oxazolyl), nitrogen substituent (e.g., amino, dimethylamino, diethylamino, piperidyl), oxygen substituent (e.g., hydroxy, methoxy, ethoxy), halogen (e.g., fluoro, chloro), sulfur substituent (e.g., methylthio, ethylthio, methanesulfonyl).

Another $R^6$ is ammonio being dimethylamine, morpholine, piperazine, pyrrolidine, piperidine, quinuchlidine, triethylenediamine, or the like aliphatic or alicyclic amino quaternalized by alkyl (e.g., methyl, ethyl, carboxymethyl, carbamoylmethyl).

Other $R^6$ is optionally substituted amino, tetrazolyl, pyrrolidyl, piperizinyl, or the like tertiary amino. The substituent can be alkyl (e.g., methyl, ethyl, amino, arylinio).

Thus, 2-halomethylcarbapenem (III) is treated with a nucleophilic reagent, for example, primary amine (e.g., optionally substituted ammonia, heterocycle substituted ammonia), secondary amine (optionally substituted pyrrolidine, piperidine, tetrazole, etc.), tertiary amine (optionally substituted quinuclidine, trialkylamine, 1-alkylpiperidine, 1-alkylpyrrolidine, etc.), heterocyclic compound (optionally substituted thiazole, pyridine, quinoline), heterocyclothiol (optionally substituted thiazolylthiol, triazolylthiol, thiadiazolylthiol, tetrazolylthiol, pyridylthiol, isoquinolylthio, etc.), or reactive derivatives thereof in a conventional manner in an inert solvent e.g. dichloromethane) at 0° C. to room temperature for 2 to 5 hours to produce 2-substituted methylcarbapenem (IV).

The compounds (IV) show potent antibacterial activity against aerobic and anaerobic Gram-positive (*Staphylococcus aureus*, etc.), and Gram-negative bacteria (*Escherichia coli, Pseudomonas aeruginosa*, etc.) and useful as human or veterinary medicines or disinfecting agents. Utilizing said antibacterial activity of compound (IV), this invention provides the following uses (1) to (4).

(1) A bactericidal or bacteriostatic method by bringing Compound (IV) to contact with a sensitive bacteria.

(2) A method for disinfecting, killing bacteria, preventing bacterial growth, and preventing perishing of a material by applying compound (IV) to a portion where sensitive bacteria are growing or supposed to grow.

(3) A method for preventing or treating an infection caused by sensitive bacteria and for promoting growth by administering compound (IV) singly or in admixture with other medicals to human or animal. For example, this invention also provides a method for treating or preventing human or veterinary bacterial infections caused by sensitive bacteria (respiratory tract infection, nasopharyngitis, rhinitis, empyema, tonsillitis, pharyngitis, bronchitis, pneumonia, pneumonitis, urinary tract infection, pyelonephritis, dermatitis, ulceration, pustulosis, abscess, ear infection, digestive tract infection, osteomyelitis, septicemia, wound and soft tissue infection, post operative infection, gynecological infection, etc.) by administering an effective amount of the said compound (I) at an effective daily dose of 0.1 to 6 gram (injection), 0.4 to 4 gram (orally), or 0.01 to 10 mg (topically).

(4) A use of compound (IV) as a starting material for producing other antibacterials and a material for sensitivity test of bacteria.

This invention also provides an antibacterial pharmaceutical formulation containing 0.01 to 99% of said compound (IV) for preventing or treating sensitive bacterial infections.

The composition of compound (IV) as a free acid, betain or light metal salt is available by formulating in a conventional manner if required with a carrier for injection (ampoule, vial, solution, or suspension for intravenous, intramuscular, or subcutaneous injection, drip, etc.), external, topical (ear-, nasal-, or eye-lotion, ointment, emulsion, spray, suppository, etc.), or oral medicine (with a enteral adsorption-promoting agent), or an activity enhancing agent (e.g., absorption or excretion controling agent, beta-lactamase inhibiting agent, other antibacterials, silastatin, etc.), or the like. The composition of compound (IV) may be solid (capsule, dry syrup, granule, lyophilized material, pellet, pill, powder, suppository, troche, tablet, etc.) or liquid (dispersion, elixir, emulsion, inhalant, injection, ointment, suspension, syrup, solution, etc.).

The capsule, granule, and tablet may be coated. They can be in a unit dosage form. The carrier is that available pharmacologically and pharmaceutically and inert to the compound (IV).

Representative examples of such carrier include, for solutions, solvent (alcohol, buffer, methyl oleate, peanut oil, sesame oil, water, etc.), buffer, dispersing agent, solubilizing agent, preservative (methyl or ethyl p-hydroxy-benzoate, sorbic acid, etc.), absorption promoter (glycerin mono- or di-octanoate, etc.), antioxidant, aromatic substance, analgesic, emulsifying agent, edible dye, stabilizing agent, suspending agent, an agent for controlling side effects or enhancing the activity (absorption or excretion controlling agent, enzymatic decomposition preventing agent, beta-lactamase inhibiting agent, other antibacterial, etc.) or the like.

The pharmaceutical preparation can be prepared conventionally.

EXAMPLES

Following Examples illustrate the embodiment of this invention. In the Examples, NMR spectra were taken at 200 Mc.

ABBREVIATIONS

Me=methyl. Et=ethyl. Bu=butyl. Ph=phenyl. PMB=p-methoxybenzyl. Ts=toluene-p-sulfonyl.

EXAMPLE 1

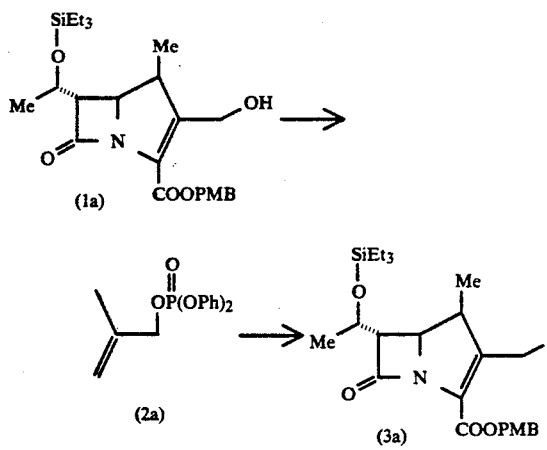

To a solution of 1β-methyl-2-hydroxymethyl-6α-(1-triethylsilyloxyethyl)-1-carba-2-penem-4-carboxylic acid p-methoxybenzyl ester (1a) (220 mg, 1 equivalents) in dichloromethane (2 ml) at $-50°$ C. are added dropwise 4-dimethylaminopyridine (62 mg, 1.1 equivalents) and diphenylphosphoric acid chloride (0.1 ml, 1.05 equivalents), and the mixture was stirred at the same temperature for 30 minutes. To the resulting solution of 1β-methyl-2-(diphenoxyphosphoryloxymethyl)-6α-(1-triethylsilyloxyethyl)-1-carba-2-penem-4-carboxylic acid p-methoxybenzyl ester (2a:TLC:silica gel, ethyl acetate:toluene=1:4, Rf=0.60) is added lithium chloride (39 mg, 2 equivalents), and the mixture is stirred for 1 hour at room temperature. The reaction mixture is diluted with cold aqueous sodium carbonate (20%, 1 ml). The separating organic layer is taken, washed with cold 0.1N-hydrochloric acid and water, and concentrated under reduced pressure to give 1β-methyl-2-chloromethyl-6α-(1-triethylsilyloxyethyl)-1-carba-2-penem-4-carboxylic acid p-methoxybenzyl ester (3a) as colorless oil. (178 mg, Yield: 78%).

NMR: δ(CDCl$_3$) ppm: 0.54~0.65(m, 6H), 0.90~1.01(m, 9H), 1.02(d, J=7.2 Hz, 3H), 1.22(d, J=6.4 Hz, 3H), 2.71~2.82(m, 1H), 2.85~3.05(m, 1H), 3.80(s, 3H), 4.20~4.42(m, 2H), 5.15, 5.40(ABq, J=14 Hz, 2H), 5.23(s, 2H), 6.87, 7.39(A$_2$B$_2$q, J=6.8 Hz, 4H).

IR: ν(CHCl$_3$) cm$^{-1}$: 2950, 1770, 1620.

EXAMPLE 2

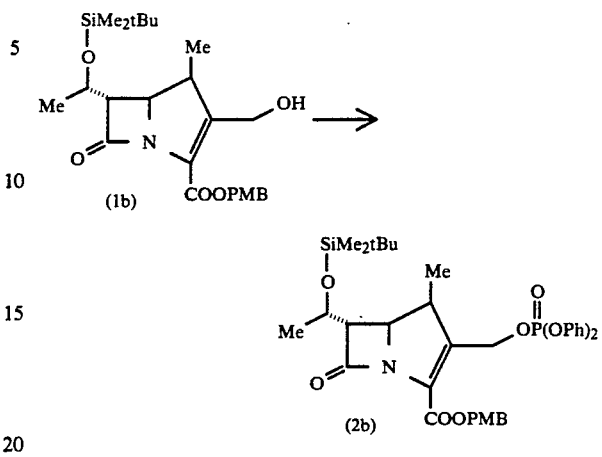

To a solution of 1β-methyl-2-hydroxymethyl-6α-(1-t-butyldimethylsilyloxyethyl)-1-carba-2-penem-4-carboxylic acid p-methoxybenzyl ester (1b) (136 mg, 1 equivalents) in dichloromethane (1 ml) at $-50°$ C. are dropwise added 4-dimethylaminopyridine (40 mg, 1.1 equivalents) and then diphenylphosphoric acid chloride (0.063 ml, 1.05 equivalents), and the mixture is stirred at the same temperature for 30 minutes. The reaction mixture is diluted with cold aqueous sodium hydrogen carbonate (20%, 1 ml) and separating organic layer is taken, washed with 0.1N cold hydrochloric acid and water, concentrated under reduced presure to give 1β-methyl-2-(diphenoxyphosphoryloxymethyl)-6α-(1-t-butyldimethylsilyloxyethyl)-1-carba-2-penem-4-carboxylic acid p-methoxybenzyl ester (2b) as pale yellow oil (190 mg, Yield: 92%).

NMR: δ(CDCl$_3$) ppm: 0.02(s, 6H), 0.89(s, 9H), 1.18(d, J=7.2 Hz, 3H), 1.30(J=6.5 Hz, 3H), 3.05~3.30(m, 2H), 4.00~4.32(m, 2H), 4.79, 5.10(ABq, J=14.2 Hz, 2H), 5.18(m, 2H), 6.86, 7.38(A$_2$B$_2$q, J=6.8 Hz, 4H), 6.90~7.50 (m, 10H).

IR: ν(CHCl$_3$) cm$^{-1}$: 2900, 1770, 1700.

EXAMPLE 3

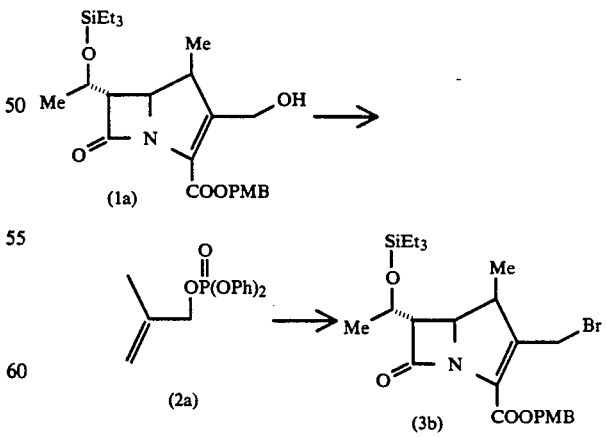

Under a condition the same with that of Example 1 or 4, 1β-methyl-2-hydroxymethyl-6α-(1-triethylsilyloxyethyl)-1-carba-2-penem-4-carboxylic acid p-methoxybenzyl ester (1a) in dichloromethane at $-50°$ C. is reacted with 4-dimethylaminopyridine (1.1 equivalents)

and diphenylphosphoric acid chloride (1.05 equivalents) for 30 minutes to give a solution of 1β-methyl-2-(diphenoxyphosphoryloxymethyl)-6α-(1-triethylsilyloxyethyl)-1-carba-2-penem-4-carboxylic acid p-methoxybenzyl ester (2a). To this solution is added dropwise a solution of sodium bromide in acetonitrile, and the mixture is stirred at 0° C. for 1 hour. The reaction mixture is worked up as before to give 1β-methyl-2-bromomethyl-6α-(1-triethylsilyloxyethyl)-1-carba-2-penem-4-carboxylic acid p-methoxybenzyl ester (3b).

TLC:silica gel, ethyl acetate:toluene=1:4. Rf=0.63.

EXAMPLE 4

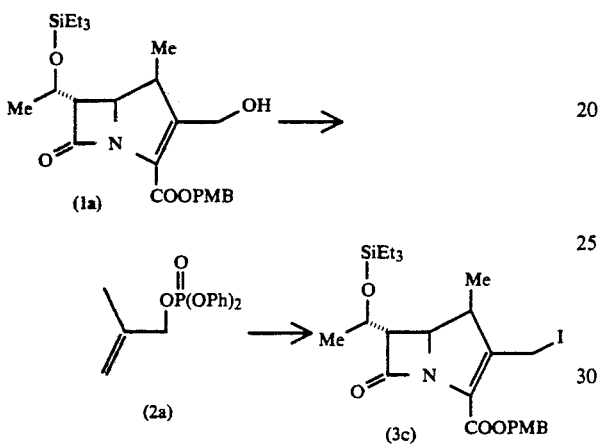

To a solution of 1β-methyl-2-hydroxymethyl-6α-(1-triethylsilyloxyethyl)-1-carba-2-penem-4-carboxylic acid p-methoxybenzyl ester (1a) (220 mg, 1 equivalents) in dichloromethane (1 ml) at −50° C. are added dropwise 4-dimethylaminopyridine (62 mg, 1.1 equivalents) and then diphenylphosphoric acid chloride (0.1 ml, 1.05 equivalents), and the mixture is stirred at the same temperature for 30 minutes. To the resulting solution of 1β-methyl-2-(diphenoxyphosphoryloxymethyl)-6α-(1-triethylsilyloxyethyl)-1-carba-2-penem-4-carboxylic acid p-methoxybenzyl ester (2a:TLC:silica gel, ethyl acetate:toluene=1:4, Rf=0.60) is added dropwise a solution of sodium iodide (139 mg, 2 equivalents) in acetonitrile (1 ml) at 0° C., and the mixture is stirred for 1 hour. After disappearance of the starting material (1a: Rf=0.27) and formation of the product (3c: Rf=0.64) by TLC (silica gel, toluene:ethyl acetate=4:1), the reaction mixture is diluted with ethyl acetate and cold aqueous sodium hydrogen carbonate (20%, 1 ml). The organic layer is taken, washed with 0.1N hydrochloric acid and water, and concentrated under reduced pressure to give 1β-methyl-2-iodomethyl-6α-(1-triethylsilyloxyethyl)-1-carba-2-penem-4-carboxylic acid p-methoxybenzyl ester (3c) as brown oil (187 mg, Yield: 69%).

NMR: δ(CDCl₃) ppm: 0.54~0.66(m, 6H), 0.88~0.98(m, 9H), 1.17(d, J=7.2 Hz, 3H), 1.22(d, J=6.4 Hz, 3H), 2.80~2.91(m, 1H), 3.15~3.30(m, 1H), 3.80(s, 3H), 4.10~4.35(m, 1H), 5.18, 5.45(ABq, J=14 Hz, 2H), 5.22(s, 2H), 6.88, 7.40(A₂B₂q, J=6.8 Hz, 4H).

IR: ν(CHCl₃) cm⁻¹: 2950, 1770, 1605.

EXAMPLE 5

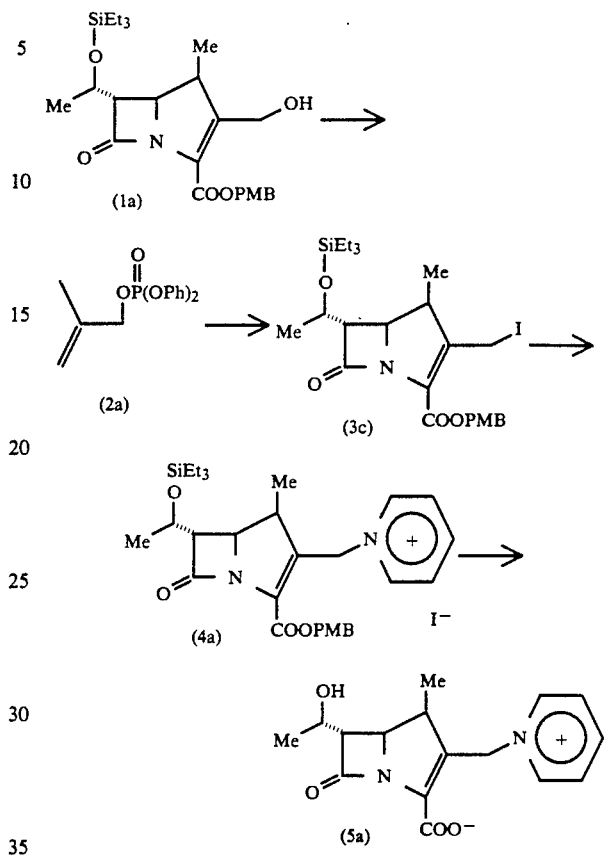

In a manner the same as above, 1β-methyl-2-iodomethyl-6α-(1-triethylsilyloxyethyl)-1-carba-2-penem-4-carboxylic acid p-methoxybenzyl ester (3c) is produced from 1β-methyl-2-hydroxymethyl-6α-(1-triethylsilyloxyethyl)-1-carba-2-penem-4-carboxylic acid p-methoxybenzyl ester (1a) (5.10 g, 1 equivalent), 4-dimethylaminopyridine (1.51 g, 1.15 equivalents), diphenylphosphoric acid chloride (2.26 ml, 1.02 equivalents), and sodium iodide (2.41 g, 1.5 equivalents). The product in the reaction mixture at 0° C. is stirred with pyridine (10 ml) at room temperature for 2 hours. The reaction mixture is diluted with ethyl acetate (200 ml) washed with water, and concentrated under reduced pressure to give residue which was wished with ether to afford 1β-methyl-2-pyridiniomethyl-6α-(1-triethylsilyloxyethyl)-1-carba-2-penem-4-carboxylic acid p-methoxybenzyl ester iodide (4a) as powder (5.76 g, Yield: 81%).

NMR: δ(CDCl₃) ppm: 0.54~0.65(m, 6H), 0.87~0.99(m, 9H), 1.20(d, J=7.2 Hz, 3H), 1.25(d, J=6.4 Hz, 3H), 3.25~3.48(m, 2H), 3.80(s, 3H), 4.18~4.32(m, 1H), 4.45(dd, J=10 Hz, J=3.0 Hz, 1H), 5.22(s, 2H), 5.70, 6.00(ABq, J=14.4 Hz, 2H), 6.90, 7.39(A₂B₂q, 4H), 7.30~9.10(m, 5H).

IR: ν(CHCl₃) cm⁻¹: 2950, 1780, 1720, 1620.

To a solution of (4a) (4.0 g, 1 equivalents) in a mixture of dichloromethane (10 ml) and anisole (5 ml) at −40° C. is added aluminum chloride (2.7 g, 3 equivalents), and the mixture is stirred at the same temperature for 2 hours. To the mixture is added sodium carbonate (2.5 g, 4.5 equivalents) in water (20 ml) and stirred under ice cooling for 10 minutes. The reaction mixture is filtered, and aqueous layer is washed with dichloromethane, purified by synthetic adsorbent, and lyophilized to give 1β-methyl-2-pyridiniomethyl-6α-(1-hydroxyethyl)-1-carba-2-penem-4-carboxylate (5a) as white powder (860 mg, Yield: 47%).

NMR: δ(D₂O) ppm: 0.90(d, J=7.4 Hz, 3H), 1.06(d, J=6.4 Hz, 3H), 2.75~2.88(m, 1H), 3.31(dd, J=6.0 Hz, J=3.0 Hz, 1H), 3.99(dd, J=8.6 Hz, J=2.8 Hz, 1H), 4.00~4.10(m, 1H), 5.20, 5.85(ABq, J=14.6 Hz, 2H), 7.86~8.74(m, 5H).

EXAMPLE 6

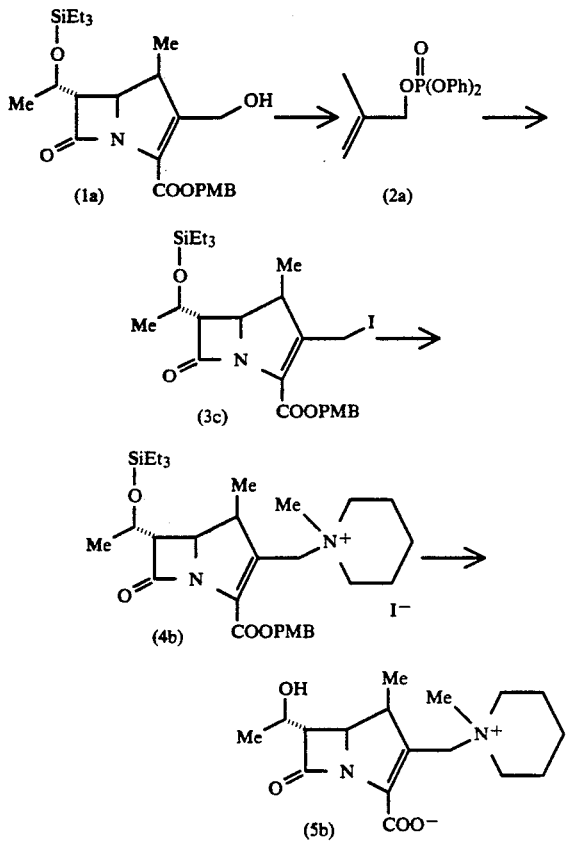

To a solution of 1β-methyl-2-hydroxymethyl-6α-(1-triethylsilyloxyethyl)-1-carba-2-penem-4-carboxylic acid p-methoxybenzyl ester (1a) (476 mg, 1 equivalents) in dichloromethane (2 ml) at −50° C. are added dropwise 4-dimethylaminopyridine (141 mg, 1.15 equivalents) and then diphenylphosphoric acid chloride (211 μl, 1.02 equivalents), and the mixture is stirred at the same temperature for 30 minutes. To the resulting solution of 1β-methyl-2-(diphenoxyphosphoryl)oxymethyl-6α-(1-triethylsilyloxyethyl)-1-carba-2-penem-4-carboxylic acid p-methoxybenzyl ester (2a:TLC:silica gel, ethyl acetate:toluene=1:4:Rf=0.60) is added dropwise a solution of sodium iodide (225 mg, 1.5 equivalents) in acetonitrile (2 ml) and the mixture is stirred for 1 hour at 0° C. To the resulting solution of 1β-methyl-2-iodomethyl-6α-(12-triethylsilyloxyethyl)-1-carba-2-penem-4-carboxylic acid p-methoxybenzyl ester (3c) is added 1-methylpiperidine (365 μl, 3 equivalents), and the misture is stirred at room temperature for 1.5 hours. The reaction mixture is diluted with ethyl acetate (10 ml), washed with water, and concentrated under reduced pressure. The residue is washed with ether to give 1β-methyl-2-(1-methylpiperidinnio-1-yl)methyl-6α-(1-triethylsilyloxyethyl)-1-carba-2-penem-4-carboxylic acid p-methoxybenzyl ester (4b) as powder (534 mg, Yield: 78%).

NMR: δ(CDCl₃) ppm: 0.53~0.65(m, 6H), 0.90~0.98(m, 9H), 1.22(d, J=6.4 Hz, 3H), 1.36(d, J=7.2 Hz, 3H), 1.50~2.05(m, 6H), 3.25~3.40(m, 2H), 3.25~3.40(m, 2H), 3.28(s, 3H), 3.35~3.6(m, 4H), 3.80(s, 3H), 4.20~4.33(m, 1H), 4.45(dd, J=10 Hz, J=3 Hz, 1H), 4.72 & 4.97(ABq, J=14 Hz, 2H), 6.90 & 7.40(A₂B₂q, J=8.6 Hz, 4H).

IR: ν(CHCl₃) cm⁻¹: 2940, 1780, 1710, 1610.

To a solution of 1β-methyl-2-(1-methylpiperidinio-1-yl)methyl-6α-(1-triethylsilyloxyethyl)-1-carba-2-penem-4-carboxylic acid p-methoxybenzyl ester (4b) (520 mg, 1 equivalents) in a mixture of dichloromethane (2 ml) and anisole (1 ml) at −40° C. is added aluminium chloride (304 mg, 3 equivalents), and the mixture is stirred for 3 hours. The reaction mixture is neutralized with sodium hydrogen carbonate (287 mg, 4.5 equivalent) and treated with synthetic polymer resin column and lyophylized to give 1β-methyl-2-(1-methylpiperidinio-1-yl)methyl-6α-(1-hydroxyethyl)-1-carba-2-penem-4-carboxylate (5b, Table II, compound 4) as white powder (125 mg, Yield: 51%).

EXAMPLE 7

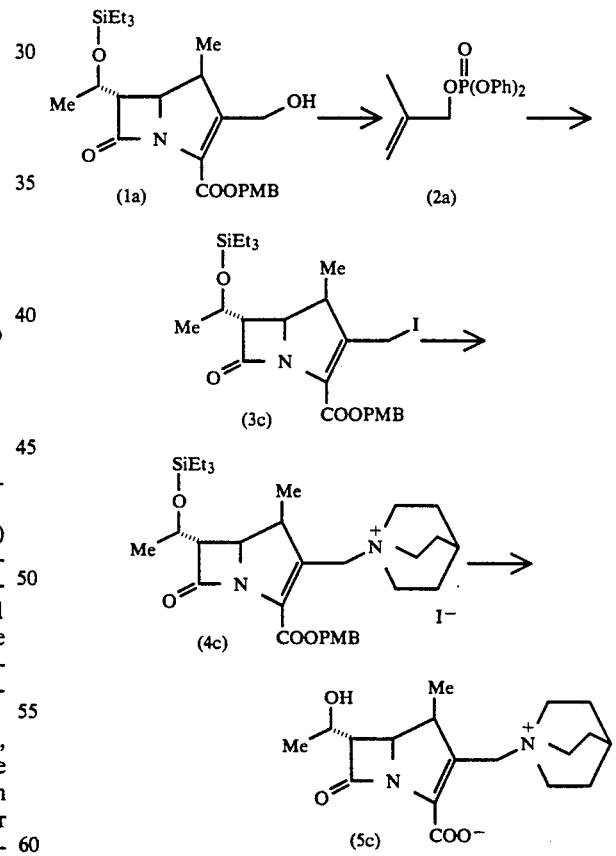

To a solution of 1β-methyl-2-hydroxymethyl-6α-(1-triethylsilyloxyethyl)-1-carba-2-penem-4-carboxylic acid p-methoxybenzyl ester (1a) (445 mg, 1 equivalents) in dichloromethane (2 ml) at −50° C. are added dropwise 4-dimethylaminopyridine (131 mg, 1.15 equivalents) and then diphenylphosphoric acid chloride (198 μl, 1.05 equivalents), and the mixture is stirred at the same temperature for 30 minutes. To the resulting solution of 1β-methyl-2-(diphenoxyphosphoryl)oxymethyl-6α-(1-triethylsilyloxyethyl)-1-carba-2-penem-4-carboxylic acid p-methoxybenzyl ester (2a:TLC:silica gel, ethyl acetate:toluene=1:4, Rf=0.60) is added dropwise a solution of sodium iodide in acetonitrile (2 ml), and the mixture is stirred at 0° C. for 1 hour. To the resulting solution of 1β-methyl-2-iodomethyl-6α-(1-triethylsilyloxyethyl)-1-carba-2-penem-4-carboxylic acid p-methoxybenzyl ester (3c) in quinuclidine (312 mg, 3 equivalents), and the mixture is stirred at room temperature for 2 hours. The reaction mixture diluted with ethyl acetate (10 ml), washed with water, and concentrated in vacuum. The residue is washed with ether to give 1β-methyl-2-(quinuclidinio-1-yl)methyl-6α-(1-triethylsilyloxyethyl)-1-carba-2-penem-4-carboxylic acid p-methoxybenzyl ester (4c) as powder (541 mg, Yield: 83%).

NMR: δ(CDCl₃) ppm: 0.53~0.65(m, 6H), 0.90~0.98(m, 9H), 1.21(d, J=6.2 Hz, 3H), 1.33(d, J=7.2 Hz, 3H), 1.97~2.22(m, 6H), 3.28~3.35(m, 1H), 3.45~3.36(m, 1H), 3.67~3.80(m, 6H), 3.81(s, 3H), 4.20~4.35(m, 1H), 4.44(dd, J=10 Hz, J=3 Hz, 1H), 4.50 & 4.73(ABq, J=14 Hz, 2H), 5.24(s, 2H), 6.90, 7.41(A₂B₂q, J=8.6 Hz, 4H).

IR: ν(CHCl₃) cm⁻¹: 2940, 1780, 1705, 1605.

To a solution of 1β-methyl-2-(quinuclidinio-1-yl)methyl-6α-(1-triethylsilyloxyethyl)-1-carba-2-penem-4-carboxylic acid p-methoxybenzyl ester (4c) (390 mg, 1 equivalent) in a mixture of dichloromethane (2 ml) and anisole (1 ml) at −40° C. are added aluminum chloride (224 mg, 3 equivalents), and the mixture is stirred at the same temperature for 2 hours. To the reaction mixture is added aqueous sodium hydrogen carbonate (221 mg, 4.5 equivalents) (10 ml), and the mixture is stirred for 10 minutes under ice cooling. The reaction mixture is filtered to remove solid, washed with dichloromethane, and treated with synthetic polymer adsorbent, and lyophlized to give 1β-methyl-2-(quinuclidinio-1-yl)-methyl-6α-(1-hydroxyethyl)-1-carba-2-penem-4-carboxylate (5c, Table II, Compound 5) as white powder (94 mg, Yield: 48%).

EXAMPLE 8

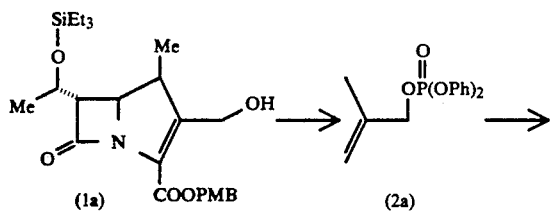

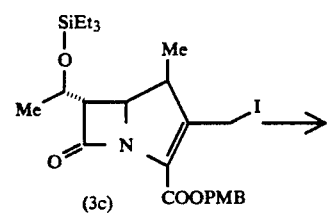

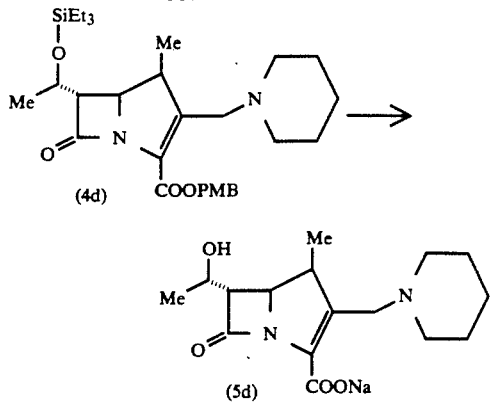

To a solution of crude 1β-methyl-2-iodomethyl-6α-(1-triethylsilyloxyethyl)-1-carba-2-penem-4-carboxylic acid p-methoxybenzyl ester (3c) [prepared from 1β-methyl-2-hydroxymethyl-6α-(1-triethylsilyloxyethyl)-1-carba-2-penem-4-carboxylic acid p-methoxybenzyl ester (1a), 1.04 g, 2.18 millimoles] in dichloromethane (17 ml) is added under ice cooling piperidine (660 ml, 3 equivalents), and the mixture is stirred for 1 hour. The reaction mixture is treated as above (extraction with ethyl acetate) and purified by silica gel chromatography (toluene:ethyl acetate=1:1) to give 1β-methyl-2-(piperidin-1-yl)methyl-6α-(1-triethylsilyloxyethyl)-1-carba-2-penem-4-carboxylic acid p-methoxybenzyl ester (4d) as powder (960 mg, Yield: 81%).

NMR: δ (CDCl₃) ppm: 0.63(q, J=6.6 Hz, 6H), 0.98(t, J=7.4 Hz, 9H), 1.18 (d, J=7.4 Hz, 3H), 1.30(d, J=6.2 Hz, 3H), 1.3~1.8(m, 6H), 2.2~2.5(m, 4H), 3.08 & 3.76(ABq, J=14.6 Hz, 2H), 3.22(dd, J=3.0 Hz, J=6.2 Hz, 1H), 3.2~3.4(m, 4H), 3.84(s, 3H), 4.1~4.2(m, 1H), 4.2~4.4(m, 1H), 5.20 & 5.28(ABq, J=12.8 Hz, 2H), 6.92 & 7.43(A₂B₂q, J=8.8 Hz, 4H).

To a solution of 1β-methyl-2-(piperidin-1-yl)methyl-6α-(1-triethylsilyloxyethyl)-1-carba-2-penem-4-carboxylic acid p-methoxybenzyl ester (4d) (815 mg, 1.5 millimole) in a mixture of dichloromethane (20 ml) and nitromethane (2 ml) and anisole (4 ml) at −40° C. is added aluminum chloride (1 g, 15 equivalents), quenched with sodium hydrogen carbonate (287 mg, 4.5 equivalents), and worked up as in Example 8 to give 1β-methyl-2-(piperidin-1-yl)methyl-6α-(1-hydroxyethyl)-1-carba-2-penem-4-carboxylic acid sodium salt (5d, Table III, Compound 5) as white powder (171 mg, Yield: 34%).

EXAMPLE 9

Under a condition similar to those of Examples 5 to 8, 2-halomethyl-1-carba-2-penem compounds (3a to 3c) is treated with the corresponding nucleophilic compound to give the compounds listed in Tables I to III.

EXAMPLE 10

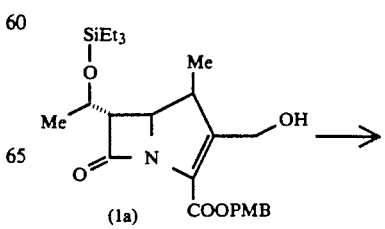

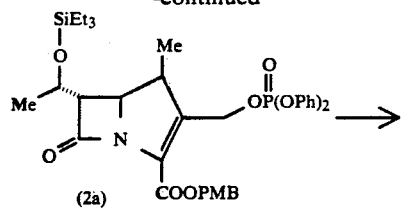

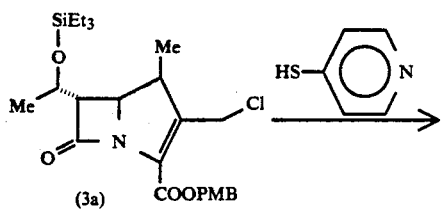

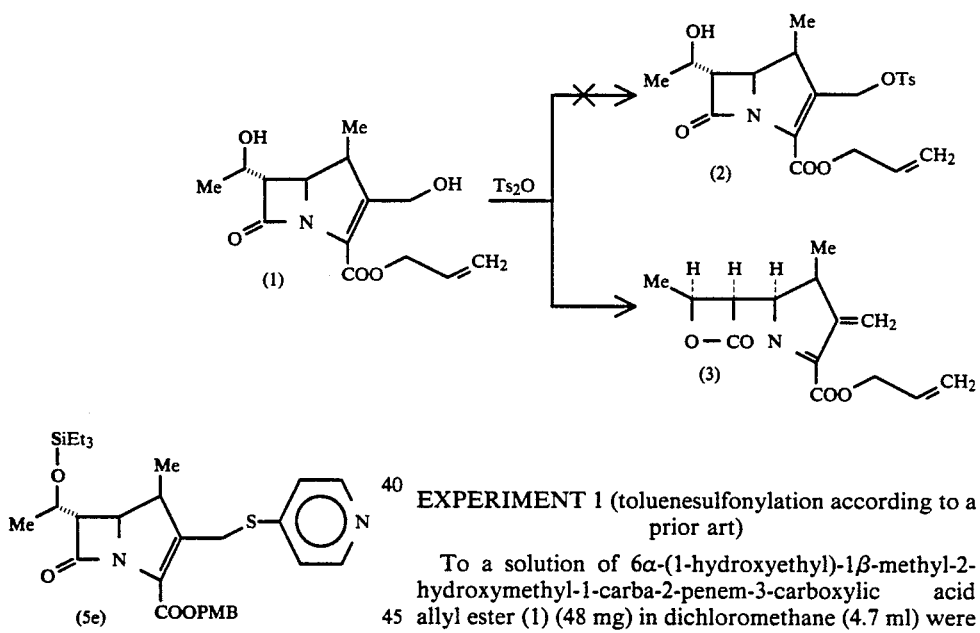

To a solution of 1β-methyl-2-(diphenoxyphosphoryloxymethyl)-6α-(1-triethylsilyloxyethyl)-1-carba-2-penem-4-carboxylic acid p-methoxybenzyl ester (2a) [prepared from 1β-methyl-2-hydroxymethyl-6α-(1-triethylsilyloxyethyl)-1-carba-2-penem-4-carboxylic acid p-methoxybenzyl ester (1a) (113 mg, 0.23 millimoles)] in dichloromethane at −30° C. is added trimethylsilyl chloride (0.033 ml, > 1.1 equivalents), and the mixture is stirred for 1 hour. The reaction mixture is poured into aqueous sodium hydrogen carbonate. The organic layer is taken, washed with aqueous saline, and concentrated under reduced pressure to give 1β-methyl-2-chloromethyl-6α-(1-triethylsilyloxyethyl)-1-carba-2-penem-4-carboxylic acid p-methoxybenzyl ester (3a) as oil (IR, 1820 cm$^{-1}$, 47 mg, Yield: ca. 40%)

To this reaction mixture of 1β-methyl-2-chloromethyl-6α-(1-triethylsilyloxyethyl)-1-carba-2-penem-4-carboxylic acid p-methoxybenzyl ester (3a) at −20° C. are added pyridinethiol (40 mg, 1.5 equivalents), acetonitrile (1 ml), and triethylamine (48 ml, 1.5 equivalents), and the mixture is stirred for 1 hour to give 1β-methyl-2-(4-pyridylthiomethyl)-6α-(1-triethylsilyloxyethyl)-1-carba-2-penem-4-carboxylic acid p-methoxybenzyl ester (5e) (94 mg, Yield: 72%).

NMR: δ (CDCl$_3$) ppm: 0.52~0.68(m, 6H), 0.85~1.00(m, 9H), 1.15(d, J=8.7 Hz, 3H), 1.23(d, J=6 Hz, 3H), 3.18(dd, J=6.0 Hz, J=2.2 Hz, 1H), 3.09~3.30(m, 1H), 3.49, 4.91(ABq, J=14.4 Hz, 2H), 3.78(s, 3H), 4.09(dd, J=13 Hz, J=2.2 Hz, 1H), 4.1~4.3(m, 1H), 5.21(s, 2H), 6.85, 7.30(A$_2$B$_2$q, J=9 Hz, 4H), 7.06, 8.30(A$_2$B$_2$q, J=6 Hz, 4H).

EXPERIMENTS

In order to functionallize the 2-methylol group of 1β-methyl-2-hydroxymethylcarbapenem (1) in a manner as disclosed in Japanese Patent Publication Kokai Sho 61-151191, Example 4 (Product (2) and those derived from it by the successive Examples have no physical constants), toluenesulfonylation is tested as follows to give product (3) in which the beta-lactam ring is cleaved.

EXPERIMENT 1 (toluenesulfonylation according to a prior art)

To a solution of 6α-(1-hydroxyethyl)-1β-methyl-2-hydroxymethyl-1-carba-2-penem-3-carboxylic acid allyl ester (1) (48 mg) in dichloromethane (4.7 ml) were added under ice cooling triethylamine (0.03 ml, 1.25 equivalents) and p-toluenesulfonic acid anhydride (66 mg, 1.14 equivalents), and the mixture was stirred at the same temperature for 1 hour. The reaction mixture was diluted with dichloromethane (20 ml), washed with phosphate buffer (pH 7, 10 ml) and saturated saline (5 ml), dried, and concentrated under reduced pressure. The residue was purified by silica gel chromatography (toluene:ethyl acetate=2:1) to give 2-(2-allyloxycarbonyl-3,3-methylene-4-methyl-1-pyrrolin-5-yl)-3-methyl-3-hydroxybutanoic acid lactone (3) (40 mg, Yield: 89%).

NMR(CDCl$_3$) δ ppm: 1.17(3H, d, J=7.3 Hz), 1.76(3H, d, J=6.5 Hz), 3.0~3.2(1H, m), 3.97 (1H, dd, J=6.1 Hz, 6.3 Hz), 4.54(1H, dd, J=4.0 Hz, J=8.0 Hz), 4.8(1H, m), 4.8~4.9(2H, m), 5.3~5.5 & 5.9~6.1(3H, m), 5.42 (1H, d, J=2.0 Hz), 6.02(1H, d, J=2.0 Hz).

IR (CHCl$_3$) cm$^{-1}$: 2950br, 1813, 1725.

EXPERIMENT 2 (MODIFIED TOSYLATION)

The failure of above tosylation might be due to side reaction at 6β-hydroxyethyl. The same reaction of silyloxyethyl (1) was also tested to give no tosylate (2).

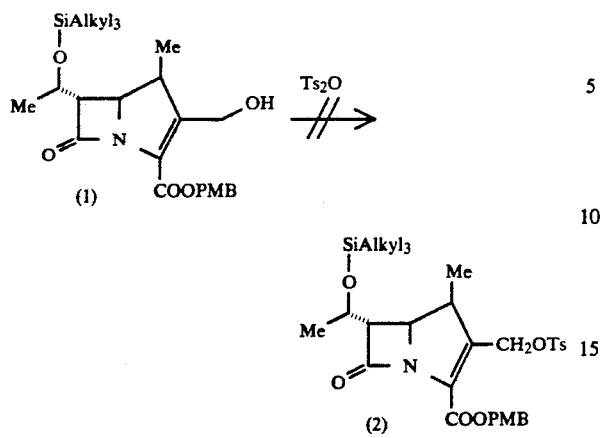

1) To a solution of 6α-(1-trimethylsilyloxyethyl)-1β-methyl-2-hydroxymethyl-1-carba-2-penem-3-carboxylic acid p-methoxybenzyl ester (1) (50 mg) in dichloromethane (3 ml) at −40° C. were added p-toluenesulfonic acid anhydride (44 mg, 1.1 equivalents) and triethylamine (0.021 ml, 1.2 equivalents), and the mixture was stired at the same temperature for 30 minutes and under ice cooling for 2 hours. The reaction mixture was tested by TLC for disappearance of the starting material. After the disappearance, the reaction mixture was diluted with dichloromethane (10 ml), washed with phosphate buffer (pH 7, 10 ml) and saturated saline (5 ml), dried, and concentrated under reduced pressure. NMR (CDCl$_3$) of the residue show no peak of the starting nor objective compounds and IR (CHCl$_3$) also showed no absorption due to betalactam ring. It was concluded that the objective 6α-(1-trimethylsilyloxyethyl)-1β-methyl-2-(p-toluenesulfonyloxymethyl)-1-carba-2-penem-3-carboxylic acid p-methoxybenzyl ester was absent.

2) The above reaction was carried out replacing triethylamine with pyridine (0.012 ml, 1.2 equivalents) to give the same result.

3) To a solution of 6α-(1-triethylsilyloxyethyl)-1β-methyl-2-hydroxymethyl-1-carba-2-penem-3-carboxylic acid p-methoxybenzyl ester (1) (143 mg) in dichloromethane (6 ml) at −35° C. were added p-toluenesulfonic anhydride (98 mg, 1 equivalent) and triethylamine (0.034 ml, 1.05 equivalents), and the mixture was stirred at the same temperature for 1 hour and under ice cooling for 2 hours. The reaction mixture showed no spot of the starting material on its TLC (silica gel, toluene:ethyl acetate=2:1) showed only spots of compounds having higher polarity and the objective 6α-(1-triethylsilyloxyethyl)-1β-methyl-2-(p-toluenesulfonyloxymethyl)-1-carba-2-penem-3-carboxylic acid p-methoxybenzyl ester could not be detected.

EXPERIMENT 3 TO 6 (TRIAL FOR SUBSTITUTION)

A trial to functionallize the 2-methylol by substituting the hydroxy with halogen failed as in the following Experiments 3 to 6.

EXPERIMENT 3

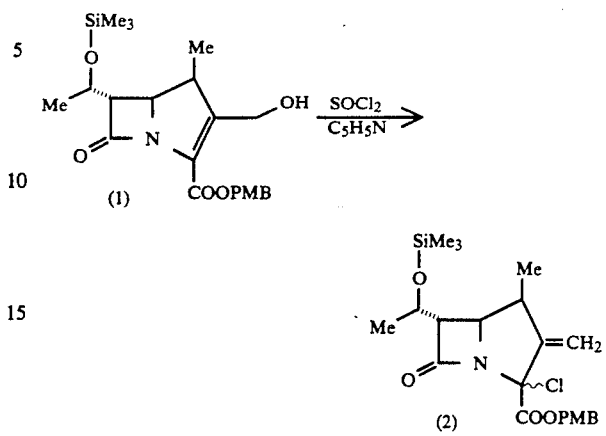

To a solution of 6α-(1-trimethylsilyloxyethyl)-1β-methyl-2-hydroxymethyl-1-carba-2-penem-3-carboxylic acid p-methoxybenzyl ester (1) (130 mg) in tetrahydrofuran (2 ml) at −30° C. were added pyridine (0.052 ml, 2 equivalents) and thionyl chloride (0.028 ml, 1.2 equivalents), and the mixture was stirred for 1 hour. The reaction mixture was diluted with ethyl acetate (10 ml), washed with saturated aqueous sodium hydrogen carbonate (5 ml) and saturated saline (5 ml), dried, and concentrated under reduced pressure. The residue is purified by silica gel chromatography (toluene:ethyl acetate=4:1) to give 6α-(1-trimethylsilyloxyethyl)-1β-methyl-2,2-methylene-3-chloro-1-carbapenam-3-carboxylic acid p-methoxybenzyl ester (3:2 mixture of isomers re position 3) (2) (92 mg, Yield: 68%).

NMR(CDCl$_3$) δ ppm: 0.02(9H, s), 1.20(3H, d, J=7.2 Hz), 1.35(3H, d, J= 7 Hz), 2.80~3.30(2H, m), 3.80(3H, s), 4.05~4.40(2H, m), 5.20(2H, s), 5.40(1H, d, J=2.5 Hz), 5.82(1H, d, J=2.5 Hz), 6.78 & 7.40(4H, A$_2$B$_2$q, J=6.8 Hz). IR (CHCl$_3$) cm$^{-1}$: 1765, 1720, 1605.

EXPERIMENT 4

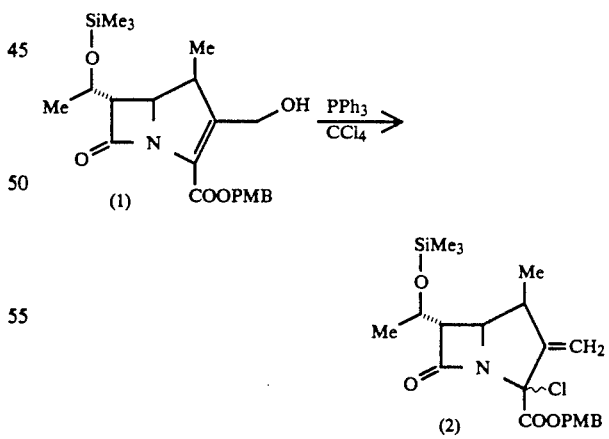

To a solution of 6α-(1-trimethylsilyloxyethyl)-1β-methyl-2-hydroxymethyl-1-carba-2-penem-3-carboxylic acid p-methoxybenzyl ester (1) (60 mg) in acetonitrile (2 ml) at room temperature were added triphenylphosphine (80 mg, 2 equivalents) and carbon tetrachloride (0.15 ml, 10 equivalents), and the mixture was stirred for 2 hours. The reaction mixture showed NMR of the product same with that of Experiment 3, i.e., 6α-(1-trimethylsilyloxyethyl)-1β-methyl-2,2-methylene-3-chloro-1-carbapenam-3-carboxylic acid p-methoxybenzyl ester (2) (3:2 mixture of isomers re position 3). Yield: ca. 70%.

IR (CHCl₃) cm⁻¹: 1820, 1720, 1630.

EXPERIMENT 5

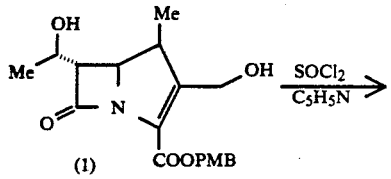

(1)

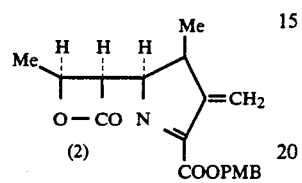

(2)

EXPERIMENT 6

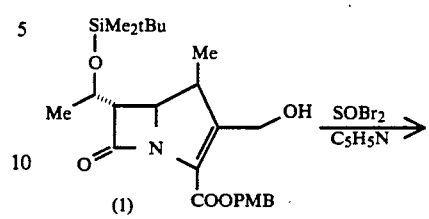

(1)

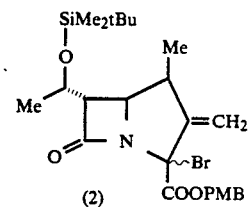

(2)

To a solution of 6α-(1-hydroxyethyl)-1β-methyl-2-hydroxymethyl-1-carba-2-penem-3-carboxylic acid p-methoxybenzyl ester (1) (120 mg) in tetrahydrofurane (2 ml) at −30° C. were added pyridine (0.053 ml, 2 equivalents) and thionyl chloride (0.029 ml, 1.2 equivalents), and the mixture was stirred for 1 hour. The reaction mixture was diluted with ethyl acetate (10 ml), washed with saturated aqueous sodium hydrogen carbonate (5 ml) and saturated saline (5 ml), dried, and concentrated under reduced pressure. The residue was purified by silica gel chromatography (toluene:ethyl acetate=2:1) to give 2-(p-methoxy-benzyloxycarbonyl-3,3-methylene-4-methylpyrrolin-5-yl)-3-methyl-3-hydroxybutyric acid lactone (2) as white crystals (67 mg). Yield: 59%.

NMR (CDCl₃) δ ppm: 1.14(3H, d, J=7.4 Hz), 1.74(3H, d, J=6.4 Hz), 3.05(1H, m), 3.81(3H, s), 3.94(1H, dd, J=6.2 Hz, J=3.0 Hz), 4.52(1H, dd, J=9.6 Hz, J=3.0 Hz), 4.83(1H, m), 5.28(2H, s), 5.38 & 5.95(2H, dd, J=2.2 Hz), 6.89 & 7.37(4H, A₂B₂q, J=6.8 Hz).

To a solution of 6α-(1-dimethyl-t-butylsilyloxyethyl)-1β-methyl-2-hydroxymethyl-1-carba-2-penem-3-carboxylic acid p-methoxybenzyl ester (1) (195 mg) in tetrahydrofuran (3 ml) at −30° C. were added pyridine (0.071 ml, 2 equivalents) and thionyl bromide (0.041 ml, 1.2 equivalents), and the mixture was stirred for 1 hour. The reaction mixture was diluted with ethyl acetate (10 ml), washed with saturated aqueous sodium hydrogen carbonate (5 ml) and saturated saline (5 ml), dried, and concentrated under reduced pressure. The residue was purified by silica gel chromatography (toluene:ethyl acetate=4:1) to give 6α-(1-dimethyl-t-butylsilyloxyethyl)-1β-methyl-2,2-methylene-3-bromo-1-carbapenam-3-carboxylic acid p-methoxybenzyl ester (2) (3:2 mixture of isomers re position 3, 138 mg. Yield: 62%).

NMR (CDCl₃) δ ppm: 0.07(6H, s), 0.89(9H, s), 1.21(3H, d, J=7.2 Hz), 1.36(3H, d, J=7.0 Hz), 2.80~3.30(2H, m), 3.80(3H, s), 4.05~4.45(2H, m), 5.20(2H, s), 5.41 & 5.85(2H, dd, J=2.5 Hz), 6.88 & 7.41(4H, A₂B₂q, J=6.8 Hz).

IR (CHCl₃) cm⁻¹: 1765, 1715, 1600.

TABLE I

Physical Constants
Arylinio Compounds

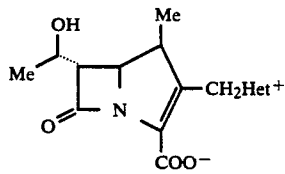

MIC: μg/ml (inoculum size = 10⁵/ml)
S = *S. aureus* Smith
E = *E. coli* EC-14
P = *Ps. aeruginosa* SR-24

| No. | Het⁺ | NMR: δ (D₂O) ppm | MIC |
|---|---|---|---|
| 1 | thiazolio-3-yl | 0.90(d, J=7.4Hz, 3H), 1.09(d, J=6.4Hz. 3H), 2.82~2.95(m, 1H), 3.31(dd, J=6.2Hz, J=3.0Hz, 1H), 4.00~4.12(m, 2H), 5.20, 5.72(ABq, J=14.8Hz, 2H), 8.00(d, J=3.6Hz, 2H), 8.25(d, J=3.6Hz, 2H), 9.50(s, 1H). | S: 0.025<br>E: 0.1<br>P: 3.13 |
| 2 | 2-aminothiazolio-3-yl | 0.91(d, J=7.2Hz, 3H), 1.10(d, J=6.4Hz, 3H), 2.80~2.92(m, 1H), 3.30(dd, J=6.2Hz, J=3.0Hz, 1H), 4.05~4.16(m, 2H), 5.15, 5.60(ABq, J=14.0Hz, 2H), 8.03(d, J=3.6Hz, 2H), 8.21 (d, J=3.6Hz, 2H). | S: 0.0125<br>E: 0.78<br>P: 6.25 |
| 3 | pyridinio-1-yl | 0.92(d, J=7.2Hz, 3H), 1.07(d, J=6.6Hz, 3H), 2.84~2.92(m, 1H), 3.33(dd, J=5.9Hz, J=3.0Hz, 1H), 3.40~4.08(m, 2H), 5.20, 5.91(ABq, J=14.6Hz, 2H), 7.88~7.95(m, 2H), 8.37~8.45(m, 1H), 8.74(d, J=5.6Hz, 2H). | S: 0.0125<br>E: 0.1<br>P: 1.56 |
| 4 | 2-methylpyridinio-1-yl | 0.97(d, J=7.4Hz, 3H), 1.08(d, J=6.3Hz, 3H), 2.63(s, 3H), 2.67~2.75(m, 1H), 3.31(d, J=6.0Hz, J=2.7Hz, 1Hz), 3.95~4.08(m, 2H), 5.11, 5.94(ABq, J=15.5Hz, 2H), 7.68~7.79(m, 2H), 8.20~8.28(m, 1H), 8.63(d, J=6.7Hz, 1H). | S: 0.025<br>E: 0.2<br>P: 3.13 |

TABLE I-continued

Physical Constants
Arylinio Compounds

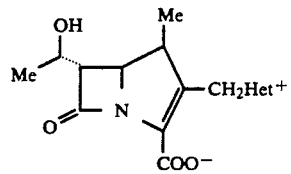

MIC: μg/ml (inoculum size = 10⁵/ml)
S = *S. aureus* Smith
E = *E. coli* EC-14
P = *Ps. aeruginosa* SR-24

| No. | Het+ | NMR: δ (D₂O) ppm | MIC |
|---|---|---|---|
| 5 | 3-methylpyridinio-1-yl | 0.91(d, J=7.3Hz, 3H), 1.07(d, J=6.4Hz, 3H), 2.36(s, 3H), 2.77-2.86(m, 1H), 3.31(dd, J=6Hz, J=3.1Hz, 1H), 4.00(dd, J=10.0Hz, J=3.1Hz, 1H), 4.02~4.08 (m, 1H), 5.11, 5.87(ABq, J=14.7Hz, 2H), 7.77(dd, J=8Hz, J=6.5Hz, 1H), 8.21 (d, J=8Hz, 1H), 8.53(d, J=5Hz, 1H), 8.54(brs, 1H). | S: 0.025 E: 0.2 P: 1.56 |
| 6 | 4-methylpyridinio-1-yl | 0.90(d, J=7.3Hz, 3H), 1.07(d, J=6.4Hz, 3H), 2.47(s, 3H), 2.79~2.87(m, 1H), 3.30(dd, J=6.0Hz, J=3.0Hz, 1H), 4.00(dd, J=6.8Hz, J=3.0Hz, 1H), 4.05~4.11 (m, 1H), 5.12, 5.78(ABq, J=14.6Hz, 2H), 7.70(A₂B₂q, J=6.6Hz, 2H), 8.51 (A₂B₂q, J=6.6Hz, 2H). | S: 0.025 E: 0.39 P: 3.13 |
| 7 | 4-ethylpyridinio-1-yl | 0.89(d, J=7.2Hz, 3H), 1.08(d, J=6.2Hz, 3H), 1.13(t, J=7.5Hz, 3H), 2.78(q, J=7.5Hz, 2H), 2.7~2.9(m, 1H), 3.30(dd, J=2.0Hz, J=6.0Hz, 1H), 3.9~4.1(m, 2H), 5.11, 5.79(ABq, J=15.0Hz, 2H), 7.72(d, J=6.4Hz, 2H), 8.53(d, J=6.4Hz, 2H). | S: 0.025 E: 0.39 P: 3.13 |
| 8 | 2,3-trimethylene-pyridinio-1-yl | 0.95(d, J=7.2Hz, 3H), 1.07(d, J=6.6Hz, 3H), 2.0~2.2(m, 2H), 2.6~2.8(m, 1H), 2.9~3.2(m, 4H), 3.30(dd, J=2.8Hz, J=6.0Hz, 1H), 3.9~4.1(m, 2H), 5.00, 5.84(ABq, J=15.2Hz, 2H), 7.57(m, 1H), 8.10(d, J=7.6Hz, 1H), 8.34(d, J=6.2Hz, 1H). | S: 0.025 E: 0.2 P: 6.25 |
| 9 | 3-aminomethyl-pyridinio-1-yl | 0.93(d, J=7.2Hz, 3H), 1.08(d, J=6.4Hz, 3H), 2.7~3.1(m, 1H), 3.34(dd, J=3.0 3.0Hz, J=6.0Hz, 1H), 4.0~4.1(m, 2H), 4.19(s, 2H), 5.23, 5.91(ABq, J=14.0Hz, 2H), 8.0(m, 1H), 8.5(m, 1H), 8.8(m, 2H). | S: 0.05 E: 0.78 P: 3.13 |
| 10 | 4-aminomethyl pyridino-1-yl | 0.91(d, J=7.2Hz, 3H), 1.08(d, J=6.4Hz, 3H), 2.74~2.99(m, 1H), 3.32(dd, J= 2.8Hz, J=6.0Hz, 1H), 3.99(s, 2H), 3.9~4.1(m, 2H), 5.17, 5.83(ABq, J=14.8Hz, 2H), 7.7~7.9(m, 2H), 8.6~8.7(m, 2H). | S: 0.05 E: 0.78 P: 3.13 |
| 11 | 3-formamidomethyl-pyridinio-1-yl | 0.86(d, J=7.4Hz, 3H), 1.09(d, J=6.4Hz, 3H), 2.8~3.0(m, 1H), 3.32(dd, J=3.2Hz, J=6.0Hz, 1H), 4.0~4.1(m, 2H), 4.42(s, 2H), 5.27, 5.81(ABq, J=14.5Hz, 2H), 7.8~8.0(m, 1H), 8.3(m, 1H), 8.7(m, 2H). | S: 0.05 E: 0.78 P: 3.13 |
| 12 | 3-(2-s-triazolyl-ethyl)pyridinio-1-yl | 0.82(d, J=7.3Hz, 3H), 1.08(d, J=6.4Hz, 3H), 2.76~2.84(m, 1H), 3.28~3.39(m, 3H), 3.99~4.08(m, 2H), 4.52(t like, 2H), 5.20, 5.73(ABq, J=14.7Hz, 2H), 7.63(A₂B₂q, J=6.7Hz, 2H), 7.84(brs, 1H), 8.11(brs, 1H), 8.59(A₂B₂q, J=6.7Hz, 2H). | S: 0.05 E: 0.78 P: 3.13 |
| 13 | 4-propionyl-pyridinio-1-yl | 0.90(d, J=7.4Hz, 3H), 1.08(d, J=6.4Hz, 3H), 1.14(t, J=7.6Hz, 3H), 2.78~ 2.90(m, 1H), 2.79(q, J=7.6Hz, 2H), 3.31(dd, J=6.0Hz, J=3.0Hz, 1H), 4.02 (dd, J=8Hz, J=3Hz, 1H), 4.03~4.09(m, 1H), 5.13, 5.80(ABq, J=14.4Hz, 2H), 7.74(A₂B₂q, J=6.6Hz, 2H), 8.55(A₂B₂q, J=6.6Hz, 2H). | S: 0.05 E: 0.76 P: 3.13 |
| 14 | 3-carbamoyl-pyridinio-1-yl | 0.93(d, J=7.3Hz, 3H), 1.07(d, J=6.5Hz, 3H), 2.85~2.94(m, 1H), 3.33(dd, J= 6.0Hz, J=3.1Hz, 1H), 4.00~4.14(m, 2H), 5.27, 5.96(ABq, J=14.8Hz, 2H), 8.00~ 8.12(m, 1H), 8.75(d, J=8.4Hz, 1H), 8.92(d, J=6.0Hz, 1H), 9.18(s, 1H). | S: 0.025 E: 0.39 P: 1.56 |
| 15 | 4-carbamoyl-pyridinio-1-yl | 0.91(d, J=7.2Hz, 3H), 1.07(d, J=6.4Hz, 3H), 2.84~2.93(m, 1H), 3.31(dd, J= 5.7Hz, J=3.0Hz, 1H), 3.99~4.08(m, 2H), 5.27, 5.94(ABq, J=14.5Hz, 2H), 8.19 (A₂B₂q, J=6.6Hz, 2H), 8.92(A₂B₂q, J=6.6Hz, 2H). | S: 0.025 E: 0.39 P: 1.56 |
| 16 | 3-(5-oxazolyl)-pyridinio-1-yl | 0.93(d, J=7.0Hz, 3H), 1.07(d, J=6.6Hz, 3H), 2.85~2.94(m, 1H), 3.32(dd, J= 6.0Hz, J=3.0Hz, 1H), 3.99~4.08(m, 2H), 5.25, 5.95(ABq, J=14.7Hz, 2H), 7.71 (s, 1H), 7.94~8.03(m, 1H), 8.23(s, 1H), 8.63~8.72(m, 1H), 9.13(s, 1H). | S: 0.025 E: 0.2 P: 1.56 |
| 17 | 4-(2-oxazolyl)-pyridinio-1-yl | 0.92(d, J=7.3Hz, 3H), 1.07(d, J=6.3Hz, 3H), 2.86~2.95(m, 1H), 3.32(dd, J= 6.0Hz, J=3.0Hz, 1H), 4.00~4.08(m, 2H), 5.23, 5.90(ABq, J=14.7Hz, 2H), 7.40 (d, J=0.8Hz, 1H), 8.04(d, J=0.8Hz, 1H), 8.36(A₂B₂q, J=7.0Hz, 2H), 8.86 (A₂B₂q, J=7.0Hz, 2H) | S: 0.025 E: 0.2 P: 3.13 |
| 18 | 4-(5-oxazolyl)-pyridinio-1-yl | 0.92(d, J=7.2Hz, 3H), 1.07(d, J=6.5Hz, 3H), 2.85~2.93(m, 1H), 3.31(dd, J= 6.0Hz, J=3.0Hz, 1H), 4.00~4.08(m, 2H), 5.17, 5.82(ABq, J=14.5Hz, 2H), 7.99 (s, 1H), 8.10(A₂B₂q, J=7.1Hz, 2H), 8.33(s, 1H), 8.71(A₂B₂q, J=7.1Hz, 2H). | S: 0.025 E: 0.39 P: 6.25 |
| 19 | 3-aminopyridinio-1-yl | 0.90(d, J=7.4Hz, 3H), 1.07(d, J=6.6Hz, 3H), 2.7~2.9(m, 1H), 3.30(dd, J=3.2Hz, J=6.0Hz, 1H), 3.9~4.1(m, 2H), 4.97, 5.72(ABq, J=15.0Hz, 2H), 7.5(m, 2H), 7.9(m, 2H). | S: 0.0125 E: 0.2 P: 1.56 |
| 20 | 4-aminopyridinio-1-yl | 0.90(d, J=7.3Hz, 3H), 1.08(d, J=6.3Hz, 3H), 2.76~2.85(m, 1H), 3.28(dd, J= 6.0Hz, J=3.1Hz, 1H), 3.99(dd, J=8.8Hz, J=3.1Hz, 1H), 4.02~4.08(m, 1H), 4.70, 4.02(ABq, J=15.1Hz, 2H), 6.68(A₂B₂q, J=5.7Hz, J=1.9Hz, 2H), 7.84 (A₂B₂q, J=5.7Hz, J=1.9Hz, 2H). | S: 0.0125 E: 0.2 P: 6.25 |
| 21 | 3,4-diamino-pyridinio-1-yl | 0.87(d, J=7.4Hz, 3H), 1.07(d, J=6.4Hz, 3H), 2.72~2.80(m, 1H), 3.27(dd, J= 5.8Hz, J=3.1Hz, 1H), 3.98(dd, J=10Hz, J=3.1Hz, 1H), 3.99~4.07(m, 1H), 4.69, 5.37(ABq, J=15Hz, 2H), 6.66(ABq, J=6.8Hz, 1H), 7.56(brs, 1H), 7.63 (ABq, J=6.8Hz, 1H). | S: 0.0125 E: 0.2 P: 3.13 |
| 22 | 4-dimethylamino-pyridinio-1-yl | 0.90(d, J=7.4Hz, 3H), 1.08(d, J=6.2Hz, 3H), 2.76~2.82(m, 1H), 3.01(s, 6H), 3.28(dd, J=6.0Hz, J=3.2Hz, 1H), 3.97~4.10(m, 2H), 4.72, 5.36(ABq, J=15Hz, 2H), 6.69, 7.86(A₂B₂q, J=7.8Hz, 4H). | S: 0.0125 E: 0.1 P: 3.13 |
| 23 | 3-hydroxypyridinio-1-yl | 0.93(d, J=7.6Hz, 3H), 1.10(d, J=6.4Hz, 3H), 2.69~2.85(m, 1H), 3.32(dd, J=5.7Hz, J=3.0Hz, 1H), 3.98~4.13(m, 2H), 4.93, 5.71(ABq, J=14.6Hz, 2H), 7.34~7.84(m, 4H). | S: 0.05 E: 0.2 P: 12.5 |
| 24 | 3-methoxypyridinio-1-yl | 0.91(d, J=7.2Hz, 3H), 1.07(d, J=6.4Hz, 3H), 2.80~2.89(m, 1H), 3.31(dd, | S: 0.025 |

TABLE I-continued

Physical Constants
Arylinio Compounds

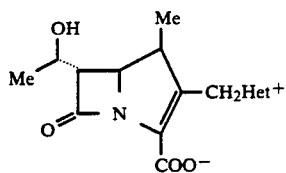

MIC: μg/ml (inoculum size = $10^5$/ml)
S = *S. aureus* Smith
E = *E. coli* EC-14
P = *Ps. aeruginosa* SR-24

| No. | Het+ | NMR: δ ($D_2O$) ppm | MIC |
|---|---|---|---|
|  |  | J=6.0Hz, J=3.1Hz, 1H), 3.84(s, 3H), 3.98~4.08(m, 2H), 5.15, 5.86(ABq, J=14.6Hz, 2H), 7.76~7.99(m, 2H), 8.34(d, J=5.8Hz, 1H), 8.45(s, 1H). | E: 0.39 P: 3.13 |
| 25 | 4-methoxypyridinio-1-yl | 0.89(d, J=7.4Hz, 3H), 1.07(d, J=6.4Hz, 3H), 2.79~2.87(m, 1H), 3.29(dd, J=5.9Hz, J=3.0Hz, 1H), 3.93(s, 3H), 3.98~4.08(m, 2H), 5.00, 5.64(ABq, J=14.8Hz, 2H), 7.28($A_2B_2$q, J=5.8Hz, 2H), 8.45($A_2B_2$q, J=5.8Hz, 2H). | S: 0.025 E: 0.39 P: 3.13 |
| 26 | 3-methylthio-pyridinio-1-yl | 0.91(d, J=7.2Hz, 3H), 1.08(d, J=6.4Hz, 3H), 2.46(s, 3H), 2.83~2.91(m, 1H), 3.32(dd, J=6Hz, J=3Hz, 1H), 4.01(dd, J=7.2Hz, J=3Hz, 1H), 4.02~4.09(m, 1H), 5.14, 5.83(ABq, J=14.6Hz, 2H), 7.74(dd, J=8.4Hz, J=5.9Hz, 1H), 8.19(d, J=8.4Hz, 1H), 8.44(d, J=5.9Hz, 1H), 8.54(s, 1H). | S: 0.0125 E: 0.39 P: 3.13 |
| 27 | 4-methylthio-pyridinio-1-yl | 0.90(d, J=7.3Hz, 3H), 1.07(d, J=6.3Hz, 3H), 2.49(s, 3H), 2.76~2.92(m, 1H), 3.29(dd, J=6.2Hz, J=3Hz, 1H), 3.98~4.10(s, 2H), 5.00, 5.66(ABq, J=14.8Hz, 2H), 7.58($A_2B_2$q, J=6.2Hz, 2H), 8.30($A_2B_2$q, J=6.2Hz, 2H). | S: 0.025 E: 0.2 P: 3.13 |
| 28 | 3-fluoropyridinio-1-yl | 0.93(d, J=7.3Hz, 3H), 1.08(d, J=6.5Hz, 3H), 2.85~2.93(m, 1H), 3.33(dd, J=5.9Hz, J=3.2Hz, 1H), 4.00~4.09(m, 2H), 5.24, 5.95(ABq, J=14.7Hz, 2H), 7.93~8.03(m, 1H), 8.25~8.33(m, 1H), 8.70(d, J=6.2Hz, 1H), 8.92(brs, 1H). | S: 0.025 E: 0.39 P: 3.13 |

Infrared Spectra:
Table I No. 3 pyridinio compound IR: ν(KBr) $cm^{-1}$: 3400 br, 1760, 1630, 1604, 1488, 1250.
Table I No. 6 4-aminopyridinio compound IR: ν(KBr) $cm^{-1}$: 3290 br, 1770, 1752, 1662, 1650, 1606, 1540, 1232, 1170.

TABLE II

Physical Constants
Aliphatic Ammonio Compounds

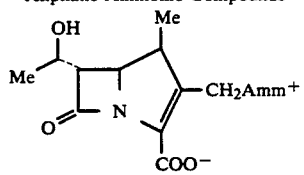

| No. | Amm+ | NMR: δ ($D_2O$) ppm | MIC |
|---|---|---|---|
| 1 | 1-methylpyrolidinio-1-yl | 0.99(d, J=7.2Hz, 3H), 1.11(d, J=6.4Hz, 3H), 2.0~2.2(m, 4H), 2.85(s, 3H), 3.1~3.4(m, 1H), 3.2~3.5(m, 4H), 3.70, 4.85(ABq, J=13.6Hz, 2H), 4.0~4.2(m, 2H). | S: 0.025 E: 0.1 P: 3.13 |
| 2 | 1-carbamoylmethyl-pyrolidinio-1-yl | 0.96(d, J=7.2Hz, 3H), 1.11(d, J=6.4Hz, 3H), 1.8~2.2(m, 4H), 3.0~3.2(m, 1H), 3.35(dd, J=2.8Hz, J=5.5Hz, 1H), 3.4~3.8(m, 4H), 3.9~4.2(m, 2H), 4.15, 4.88(ABq, J=13.8Hz, 2H), 4.1~4.3(m, 2H). | S: 0.1 E: 0.2 P: 12.5 |
| 3 | 1-sodiooxycarbonyl-methylpyrolidinio-1-yl | 0.91(d, J=7.2Hz, 3H), 1.09(d, J=6.4Hz, 3H), 1.8~2.1(m, 4H), 2.9~3.2(m, 1H), 2.9~3.2(m, 4H), 3.32(dd, J=3.0Hz, J=5.8Hz, 1H), 3.55(s, 2H), 3.66, 3.83(ABq, J=16.8Hz, 2H), 4.0~4.1(m, 2H). | S: 0.39 E: 0.39 P: 50 |
| 4 | 1-methylpiperidinio-1-yl | 1.01(d, J=7.2Hz, 3H), 1.12(d, J=6.4Hz, 3H), 1.40~1.80(m, 6H), 2.86(s, 3H), 3.10~3.20(dd, J=6.0Hz, J=3.2Hz, 1H), 3.15~3.30(m, 4H), 3.70, 4.73(ABq, J=13.4Hz, 2H), 4.05~4.20(ABq, J=13.4Hz, 2H). | S: 0.025 E: 0.1 P: 3.13 |
| 5 | quinuclidinio-1-yl | 0.95(d, J=7Hz, 3H), 1.12(d, J=6.4Hz, 3H), 1.75~2.05(m, 7H), 3.10~3.30(m, 6H), 3.15~3.35(m, 2H), 3.50, 4.55(ABq, J=13.8Hz, 2H), 4.05~4.15(m, 2H). | S: 0.025 E: 0.2 P: 6.25 |
| 6 | triethylenedi-ammonio-1-yl | 0.97(d, J=7.2Hz, 3H), 1.25(d, J=6.4Hz, 3H), 2.90~3.30(m, 12H), 3.15(m, 1H), 3.37(dd, J=6.0Hz, J=3.2Hz, 1H), 3.65, 4.75(ABq, J=13.2Hz, 2H), 4.05~4.20(m, 2H). | S: 0.1 E: 0.39 P: 6.25 |

TABLE III

Physical Constants
Amino Compounds

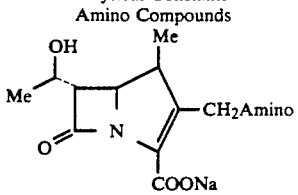

| No. | Amino | NMR: δ(D$_2$O) ppm | MIC |
|---|---|---|---|
| 1 | pyridinio-1-ylamino (COOR$^5$=COO) | 0.91(d, J=7.2Hz, 3H), 1.10(d, J=6.4Hz, 3H), 3.09~3.17(m, 1H), 3.25(dd, J=5.9Hz, J=2.9Hz, 1H), 3.94, 4.49(ABq, J=14.3Hz, 2H), 3.97~4.08(m, 2H), 7.85~7.92(m, 2H), 8.29~8.36(m, 1H), 8.64~8.67(m, 2H). | S: 0.025<br>E: 0.39<br>P: 12.5 |
| 2 | pyrolidin-1-yl | 0.99(d, J=7.4Hz, 3H), 1.10(d, J=6.4Hz, 3H), 1.9(m, 4H), 2.9~3.3(m, 1H), 2.9~3.3(m, 4H), 3.00(dd, J=2.8Hz, J=6Hz, 1H), 3.90(s, 2H), 4.0~4.1(m, 2H). | S: 0.0125<br>E: 0.39<br>P: 12.5 |
| 3 | 3-aminopyrolidin-1-yl | 0.95(d, J=7.4Hz, 3H), 1.10(d, J=6.4Hz, 3H), 2.9~3.1(m, 1H), 3.26(dd, J=2.8Hz, J=6.2Hz, 1H), 3.43, 3.63(broad ABq, J=13.6Hz, 2H), 4.0~4.1(m, 2H). | S: 0.05<br>E: 0.78<br>P: 3.13 |
| 4 | piperidin-1-yl | 0.98(d, J=7.0Hz, 3H), 1.10(d, J=6.2Hz, 3H), 1.2~1.9(m, 6H), 2.5~3.5(m, 4H), 2.9~3.1(m, 1H), 3.29(dd, J=3Hz, J=6Hz, 1H), 3.67, 3.79(ABq, J=15.2Hz, 2H), 4.0~4.1(m, 2H). | S: 0.0125<br>E: 1.56<br>P: 50 |
| 5 | 2-methyltetrazol-2-yl | 0.92(d, J=7.4Hz, 3H), 1.07(d, J=6.2Hz, 3H), 2.336(s, 3H), 2.6~2.7(m, 1H), 3.28 (dd, J=3.0Hz, J=7.0Hz, 1H), 3.9~4.1(m, 2H), 5.28, 5.97(ABq, J=14.0Hz, 2H). | S: 0.05<br>E: 0.78<br>P: 12.5 |

Infrared Spectra:
Table III No. 1 pyridinio-1-ylamino compound IR: ν(KBr) cm$^{-1}$: 3400, 3110, 2960, 1750, 1590, 1260.

What we claim is:

1. A process for preparing 2-halomethylcarbapenem (III) which comprises treating 2-hydroxymethylcarbapenem (I) with a phosphorylating reagent to give 2-phosphoryloxymethylcarbapenem (II) and then treating this product with a halogenating reagent.

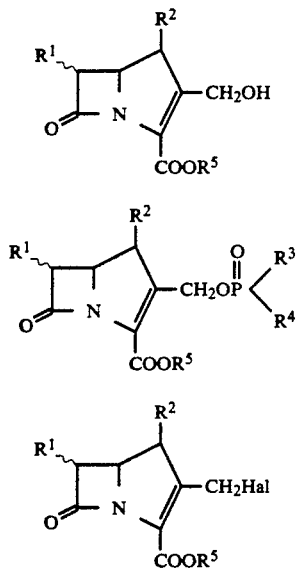

wherein,
R$^1$ is hydrogen or substituted or unsubstituted alkyl;
R$^2$ is hydrogen or substituted or unsubstituted alkyl;
R$^3$, R$^4$ is halogen or substituted or unsubstituted alkoxy or aryloxy;
R$^5$ is hydrogen or carboxy protecting group; and
Hal is halogen.

2. A process as claimed in claim 1 wherein 2-hydroxymethylcarbapenem (I) is treated with 1 to 5 equivalents of the phosphorylating reagent in the presence of 0 to 2 equivalents of the acid scavenger in an aprotic solvent at −60° to −20° C. for 30 minutes to 3 hours to give 2-phosphoryloxymethylcarbapenem (II).

3. A process as claimed in claim 2 wherein the phosphorylating reagent is a halogenide of phosphoric acid derivatives in which 2 of hydroxys in phosphoric acid is substituted by halogen, substituted or unsubstituted alkoxy or aryloxy.

4. A process as claimed in claim 2 wherein the acid scavenger for phosphorylation of the acid scavenger is an oxide, hydroxide, carbonate, bicarbonate, of alkali metal, alkaline earth metal.

5. A process as claimed in claim 1 wherein the 2-phosphoryloxymethylcarbapenem (II) is treated with a halogenating reagent to give 2-halomethylcarbapenem (III) at −40° C. to room temperature for 30 minutes to 3 hours.

6. A process as claimed in claim 5 wherein the halogenating reagent is a halide of alkali metal or alkaline earth metal, tri-lower alkylsilyl halide, di-lower alkylsilyl dihalide, mono-lower alkylsilyl halide, silane tetrahalide, tri-lower alkylstannic halide, or di-lower alkylstannic dihalide.

7. A process as claimed in claim 6 wherein the halide is chloride, bromide, or iodide.

8. A process for preparing 2-phosphoryloxymethylcarbapenem (II) which comprises treating 2-hydroxymethylcarbapenem (I) with a phosphorylating reagent.

9. A process for preparing 2-halomethylcarbapenem (III) which comprises treating 2-phosphoryloxymethylcarbapenem (II) with a halogenating reagent.

* * * * *